United States Patent
Kitagawa et al.

(10) Patent No.: US 11,598,548 B2
(45) Date of Patent: *Mar. 7, 2023

(54) DEVICE FOR ESTIMATING DROWSINESS OF A USER BASED ON IMAGE AND ENVIRONMENT INFORMATION

(71) Applicant: DAIKIN INDUSTRIES, LTD., Osaka (JP)

(72) Inventors: Keita Kitagawa, Osaka (JP); Takuya Kazusa, Osaka (JP); Youichi Handa, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 421 days.

This patent is subject to a terminal disclaimer.

(21) Appl. No.: 16/755,242

(22) PCT Filed: Aug. 23, 2018

(86) PCT No.: PCT/JP2018/031081
§ 371 (c)(1),
(2) Date: Apr. 10, 2020

(87) PCT Pub. No.: WO2019/087536
PCT Pub. Date: May 9, 2019

(65) Prior Publication Data
US 2020/0240670 A1  Jul. 30, 2020

(30) Foreign Application Priority Data

Oct. 30, 2017 (JP) .............................. JP2017-209733

(51) Int. Cl.
*F24F 11/76* (2018.01)
*F24F 11/80* (2018.01)
(Continued)

(52) U.S. Cl.
CPC ............ *F24F 11/76* (2018.01); *A61B 5/4806* (2013.01); *A61B 5/4809* (2013.01); *F24F 11/30* (2018.01);
(Continued)

(58) Field of Classification Search
CPC ............ F24F 11/76; F24F 11/80; F24F 11/30; A61M 21/02
(Continued)

(56) References Cited

U.S. PATENT DOCUMENTS

2012/0212353 A1* 8/2012 Fung ..................... B60W 10/04
701/1
2015/0216466 A1  8/2015 Kronberg et al.
(Continued)

FOREIGN PATENT DOCUMENTS

CN          106361270 A    2/2017
JP          8-332871 A     12/1996
(Continued)

OTHER PUBLICATIONS

International Search Report, issued in PCT/JP2018/031081, PCT/ISA/210, dated Oct. 9, 2018.

*Primary Examiner* — Md Azad
(74) *Attorney, Agent, or Firm* — Birch, Stewart, Kolasch & Birch, LLP

(57) ABSTRACT

A camera (26) takes an image of at least one user (U1, U2, U3). A room environment information sensor (13) senses room environment information relating to an environment of a room (r1) in which the at least one user (U1, U2, U3) is present. The estimator (66) estimates a drowsiness condition of the at least one user (U1, U2, U3) based on the image of the at least one user (U1, U2, U3) taken by the camera (26) and the room environment information sensed by the room environment information sensor (13).

14 Claims, 9 Drawing Sheets

(51) Int. Cl.
 *F24F 11/30* (2018.01)
 *A61B 5/00* (2006.01)
 *A61M 21/02* (2006.01)

(52) U.S. Cl.
 CPC .............. *F24F 11/80* (2018.01); *A61B 5/4812* (2013.01); *A61B 5/4821* (2013.01); *A61M 21/02* (2013.01)

(58) Field of Classification Search
 USPC ........................................................ 700/258
 See application file for complete search history.

(56) References Cited

U.S. PATENT DOCUMENTS

| | | | |
|---|---|---|---|
| 2015/0351681 A1* | 12/2015 | Lee .................... | G08B 21/06 600/595 |
| 2016/0046294 A1* | 2/2016 | Lee .................... | B60K 28/06 340/576 |
| 2016/0363340 A1 | 12/2016 | Shikii et al. | |
| 2017/0020432 A1 | 1/2017 | Kusukame et al. | |
| 2019/0290180 A1* | 9/2019 | Kusukame .......... | A61B 5/0878 |
| 2020/0330047 A1 | 10/2020 | Kusukame et al. | |

FOREIGN PATENT DOCUMENTS

| | | |
|---|---|---|
| JP | 2005-104237 A | 4/2005 |
| JP | 2009-201676 A | 9/2009 |
| JP | 2016-217709 A | 12/2016 |
| JP | 2017-127616 A | 7/2017 |
| TW | I596462 B | 8/2017 |

\* cited by examiner

FIG.3

| USER IDENTIFICATION INFORMATION | MOVEMENT/CONDITION OF USER | DROWSINESS CONDITION |
|---|---|---|
| U1 | LEANING BODY TO RIGHT OR LEFT/ SLOW IN MOVEMENT/ RESTING CHEEK ON HAND/ STRETCHING BODY/ CLOSING EYES | DROWSY |
| U2 | EYES ARE OPEN/ ACTIVE IN MOVEMENT/ MOVING HANDS | NOT DROWSY |
| ... | ... | ... |

63

DEVICE FOR ESTIMATING DROWSINESS OF A USER BASED ON IMAGE AND ENVIRONMENT INFORMATION

TECHNICAL FIELD

The present invention relates to a drowsiness estimation device.

BACKGROUND ART

As shown in Patent Document 1, a technique for detecting a driver's fatigue condition from a camera and the movement of a handle has been known.

CITATION LIST

Patent Document

PATENT DOCUMENT 1: Japanese Unexamined Patent Publication No. 2005-104237

SUMMARY OF THE INVENTION

Technical Problem

Drowsiness of a user, such as a driver, may be caused not only by the user's fatigue but also by other factors. It is difficult for the technique of Patent Document 1 to determine how drowsy the user is.

It is an object of the present invention to accurately determine a user's drowsiness condition.

Solution to the Problem

A first aspect of the present disclosure is directed to a drowsiness estimation device including: an imager (26) configured to take an image of at least one user (U1, U2, U3); a sensor (13) configured to sense room environment information relating to an environment of a room (r1) in which the at least one user (U1, U2, U3) is present; and an estimator (66) configured to estimate a drowsiness condition of the at least one user (U1, U2, U3), based on the image of the at least one user (U1, U2, U3) taken by the imager (26) and the room environment information sensed by the sensor (13).

Examples of the room environment information include the $CO_2$ concentration and the temperature in the room. Such room environment information may be a factor affecting the drowsiness condition of the user. Here, taking an image of the user allows the user's drowsiness information to be estimated based on the image and the room environment information. Thus, the drowsiness condition of the user can be accurately determined.

A second aspect of the present disclosure is an embodiment of the first aspect. In the second aspect, the image shows a movement of the at least one user (U1, U2, U3) representing the drowsiness condition of the at least one user (U1, U2, U3) and/or a condition of the at least one user (U1, U2, U3) representing the drowsiness condition of the at least one user (U1, U2, U3), and the estimator (66) extracts the movement of the at least one user (U1, U2, U3) and/or the condition of the at least one user (U1, U2, U3) from the image, and estimates the drowsiness condition of the at least one user (U1, U2, U3).

Thus, the drowsiness condition indicating how drowsy the user is is more accurately estimated.

A third aspect of the present disclosure is an embodiment of the first or second aspect. In the third aspect, the estimator (66) determines sex and/or age of the at least one user (U1, U2, U3) from the image, and further estimates the drowsiness condition of the at least one user (U1, U2, U3) based on the determined sex and/or age of the at least one user (U1, U2, U3).

This further improves the accuracy with which the drowsiness conditions of the users are estimated.

A fourth aspect of the present disclosure is an embodiment of any one of the first to third aspects. In the fourth aspect, the device further includes: a surface temperature measurer (128) configured to measure a surface temperature of the at least one user (U1, U2, U3) present in the room (r1), wherein the estimator (66) further estimates the drowsiness condition of the at least one user (U1, U2, U3), based on a result measured by the surface temperature measurer (128).

This further improves the accuracy with which the drowsiness conditions of the users are estimated.

A fifth aspect of the present disclosure is an embodiment of any one of the first to fourth aspects. In the fifth aspect, an air conditioner (10) is mounted on a ceiling of the room (r1), and the imager (26) is provided for the air conditioner (10).

This allows the imager (26) to take an image of the user in the room while the possibility that the user may be blocked by an obstacle is low.

A sixth aspect of the present disclosure is an embodiment of any one of the first to fifth aspects. In the sixth aspect, if the at least one user (U1, U2, U3) includes a plurality of users (U1, U2, U3) present in the room (r1), the estimator (66) estimates the drowsiness condition of each of the plurality of users (U1, U2, U3).

A seventh aspect of the present disclosure is an embodiment of the sixth aspect. In the seventh aspect, the device further includes: a storage unit (62) configured to store user information (63) about each of the plurality of users (U1, U2, U3), the user information (63) including the movement and/or the condition of the user (U1, U2, U3) and the drowsiness condition of the user (U1, U2, U3) who is making the movement and/or who is in the condition, the drowsiness condition being associated with the movement and/or the condition of the user (U1, U2, U3), wherein the estimator (66) extracts the movement and/or the condition of each of the users (U1, U2, U3) from the image, and estimates the drowsiness condition of each of the users (U1, U2, U3) using the extracted result and the user information (63).

This further improves the accuracy with which the drowsiness conditions of the individual users are estimated.

An eighth aspect of the present disclosure is an embodiment of any one of the first to seventh aspects. In the eighth aspect, the device further includes: a receiver (30) capable of receiving an entry, by the at least one user (U1, U2, U3), of drowsiness information indicating the drowsiness condition of the at least one user (U1, U2, U3); and a model updater (68) configured to make an estimation model (67) learn based on the image taken by the imager (26) and/or the drowsiness information received by the receiver (30), the estimation model (67) being used to estimate the drowsiness condition.

Thus, performing an operation for estimating the drowsiness condition using the estimation model that has learned further improves the accuracy with which the drowsiness condition of the user is estimated.

A ninth aspect of the present disclosure is an embodiment of any one of the first to seventh aspects. In the ninth aspect, the device further includes: a control unit (14) configured to control a first air-conditioning operation of the air conditioner (10) for conditioning air in the room (r1), based on a result estimated by the estimator (66) so that a level of the drowsiness condition of the at least one user (U1, U2, U3) decreases.

This improves the drowsiness condition of the user present in the room. As a result, the user is more easily awakened.

A tenth aspect of the present disclosure is an embodiment of the ninth aspect. In the tenth aspect, the device further includes: a model updater (68) configured to determine the actual drowsiness condition of the at least one user (U1, U2, U3) based on the image taken by the imager (26) after the first air-conditioning operation performed based on the result estimated by the estimator (66), and make the estimation model (67) learn based on a result of the determination, the estimation model (67) being used to estimate the drowsiness condition.

This further improves the accuracy of the estimation model so that the result estimated by the estimation model matches the actual drowsiness condition as much as possible. Performing an operation for estimating the drowsiness condition using the estimation model that has learned further improves the accuracy with which the drowsiness condition of the user is estimated.

An eleventh aspect of the present disclosure is an embodiment of the ninth or tenth aspect. In the eleventh aspect, the device further includes: a model updater (68) configured to make the estimation model (67) learn based on a change in a movement and a condition of the at least one user (U1, U2, U3) by which movement and condition the drowsiness of the at least one user (U1, U2, U3) has been determined, as a result of comparison between the image taken by the imager (26) before the first air-conditioning operation performed based on the result estimated by the estimator (66) and another image taken by the imager (26) after the first air-conditioning operation, the estimation model (67) being used to estimate the drowsiness condition.

This further improves the accuracy of the estimation model so that the result estimated by the estimation model matches the actual drowsiness condition as much as possible. Performing an operation for estimating the drowsiness condition using the estimation model that has learned further improves the accuracy with which the drowsiness condition of the user is estimated.

A twelfth aspect of the present disclosure is an embodiment of the eleventh aspect. In the twelfth aspect, the change in the movement and the condition by which the drowsiness of the at least one user (U1, U2, U3) has been determined means that a frequency of the movement and the condition decreases or that the movement and the condition are not observed.

Thus, whether or not the result estimated by the estimation model matches the actual drowsiness condition can be more accurately determined.

A thirteenth aspect of the present disclosure is an embodiment of any one of the ninth to twelfth aspects. In the thirteenth aspect, the device further includes: a receiver (30) capable of receiving an entry, by the at least one user (U1, U2, U3), of drowsiness information indicating the drowsiness condition of the at least one user (U1, U2, U3), wherein the control unit (14) learns details of control of the first air-conditioning operation, based on the drowsiness information received by the receiver (30) after the first air-conditioning operation performed based on the result estimated by the estimator (66), so that the level of the drowsiness condition of the at least one user (U1, U2, U3) decreases.

This makes it easier for the first air-conditioning operation performed next time to lower the drowsiness level of the user (U1, U2, U3).

A fourteenth aspect of the present disclosure is an embodiment of any one of the ninth to thirteenth aspects. In the fourteenth aspect, the control unit (14) learns details of control of the first air-conditioning operation, based on the image taken by the imager (26) after the first air-conditioning operation performed based on the result estimated by the estimator (66), so that the level of the drowsiness condition of the at least one user (U1, U2, U3) decreases.

This makes it easier for the first air-conditioning operation performed next time to lower the drowsiness level of the user (U1, U2, U3).

A fifteenth aspect of the present disclosure is an embodiment of the thirteenth or fourteenth aspect. In the fifteenth aspect, the details of control of the first air-conditioning operation include adjusting at least one of a rotational speed of an indoor fan (12) of the air conditioner (10), a position of a flap (16) configured to adjust an airflow direction of air blown from the air conditioner (10), a set temperature of the air conditioner (10), or a target $CO_2$ concentration in the room (r1).

This makes it easier for the first air-conditioning operation performed next time to more reliably lower the drowsiness level of the user (U1, U2, U3).

ADVANTAGES OF THE INVENTION

According to the aspects of the present disclosure, the drowsiness of a user can be accurately determined.

BRIEF DESCRIPTION OF THE DRAWINGS

FIG. 3 is a conceptual diagram of user information.

DESCRIPTION OF EMBODIMENTS

Embodiments of the present disclosure will be described in detail with reference to the drawings. The following embodiments are merely exemplary ones in nature, and are not intended to limit the scope, applications, or use of the present invention.

First Embodiment

<Outline>

Figure 1:
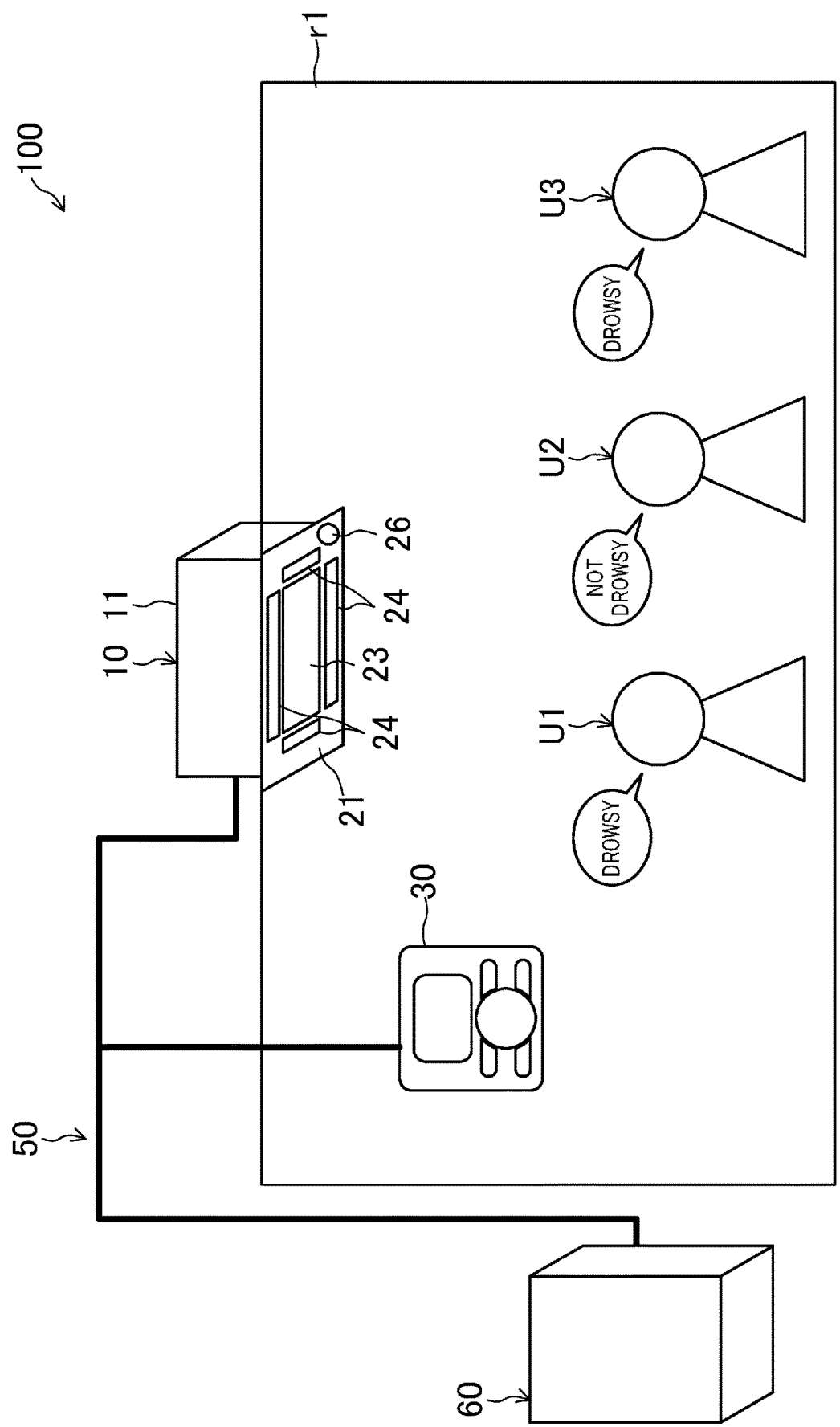
FIG. 1 shows the external appearance of an air-conditioning system including a drowsiness estimation device.
Figure 2:
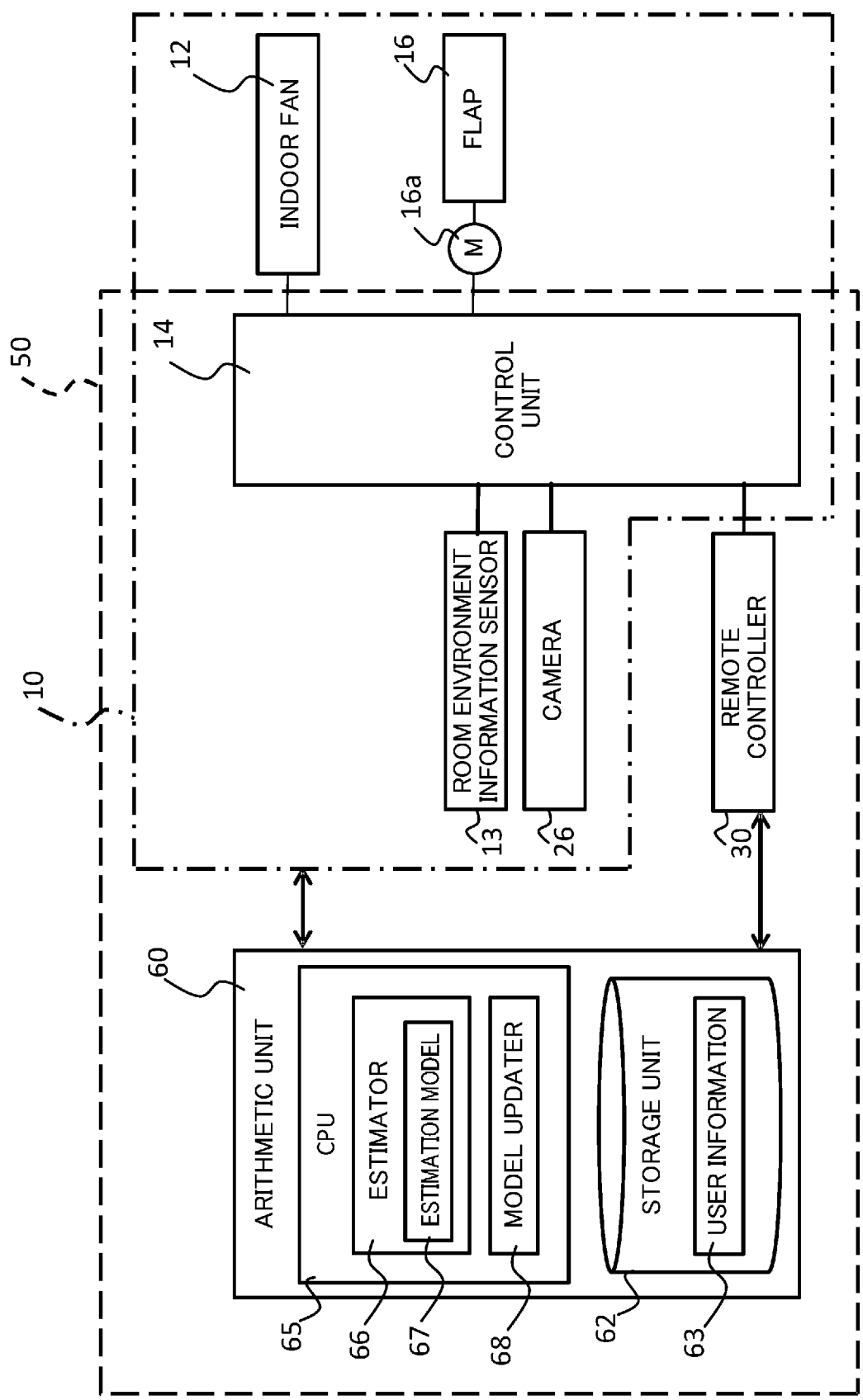
FIG. 2 is a block diagram schematically showing a configuration of an air-conditioning system including a drowsiness estimation device.

FIG. 1 shows the external appearance of an air-conditioning system (100) including an air-conditioning controller (50) (equivalent to a drowsiness estimation device) according to this embodiment. As shown in FIGS. 1 and 2, the air-conditioning controller (50) includes some of components of an air conditioner (10), a remote controller (30) (equivalent to a receiver), and an arithmetic unit (60).

As shown in FIG. 1, the air conditioner (10) is provided in a room (r1) to be air-conditioned, and conditions air in the room (r1). The remote controller (30) is not only used to set a target temperature and a target humidity of air to be conditioned by the air conditioner (10), but also used in order that any one of users (U1, U2, U3) may operate the remote controller (30) to directly instruct the air conditioner (10) which of operating modes of the air conditioner (10) should be selected and whether the air conditioner (10) should turn on or off.

The air-conditioning controller (50) controls an air-conditioning operation of the air conditioner (10). In particular, the air-conditioning controller (50) according to this embodiment estimates the drowsiness conditions of the users (U1, U2, U3) using an image showing the users (U1, U2, U3) present in the room (r1), and controls the air-conditioning operation (equivalent to a first air-conditioning operation) of the air conditioner (10) based on the estimated drowsiness conditions, thereby providing an environment that improves the drowsiness conditions of the users (U1, U2, U3).

<Configuration of Air Conditioner>

The air conditioner (10) is a ceiling-mounted air conditioner, and has a body (11) embedded in the ceiling of the room (0). A lower surface (21) of the body (11) is exposed to the room (r1), and has an air inlet (23) through which air is sucked into the body (11), and an air outlet (24) through which air is blown out of the body (11) into the room (r1).

A camera (26) (equivalent to an imager) is provided on the lower surface (21) of the body (11).

The camera (26) has a lens (not shown) facing downward of the air conditioner (10) to take an image of the users (U1, U2, U3) present in the room (r1). The image may be a dynamic image of the users (U1, U2, U3), or may be still images of the users (U1, U2, U3) successively taken. However, a situation where the image is a dynamic image is exemplified here. The image taken by the camera (26) shows movements and conditions (including facial expressions) of the users (U1, U2, U3) representing the drowsiness conditions of the users (U1, U2, U3). If a user (U1, U2, U3) feels drowsy, the user makes the following movements and is in the following conditions, such as leaning the body to the right or left, being slow in movement, resting a cheek on one of their hands, stretching the body, closing the eyes, and so on. In contrast, if a user (U1, U2, U3) does not feel drowsy, the user makes the following movements or is in the following conditions, such as being active in movement, opening the eyes, manually performing an operation, and so on. The camera (26) takes an image of such movements or the like of the users (U1, U2, U3) as an image indicating the drowsiness conditions of the users (U1, U2, U3).

The body (11) of the air conditioner (10) includes therein a heat exchanger (not shown) configured to exchange heat between air sucked through the inlet (23) into the body (11) and a refrigerant, an indoor fan (12) configured to supply the air that has exchanged heat with the refrigerant through the outlet (24) into the room (r1), an airflow direction adjusting flap (16) provided at the outlet (24), and a motor (16a) connected to a shaft of the flap (16) and serving as a drive source to change the direction of the flap (16) (see FIG. 2).

Further, the body (11) includes therein a room environment information sensor (13) (equivalent to a sensor), and a control unit (14).

The room environment information sensor (13) senses room environment information relating to the environment of the room (r1), and is a suction sensor provided near the inlet (23). Examples of the room environment information include the temperature, humidity, and $CO_2$ concentration of air in the room (r1) sucked through the inlet (23).

The control unit (14) is a microcomputer including a CPU and a memory. The control unit (14) is electrically connected to the indoor fan (12), the motor (16a) for the flap (16), the room environment information sensor (13), the camera (26), and other components. The control unit (14) is connected to both the remote controller (30) and the arithmetic unit (60) so as to be capable of communicating with the remote controller (30) and the arithmetic unit (60).

The control unit (14) controls how the indoor fan (12), the motor (16a) for the flap (16), and other components are driven, based on the results sensed by the room environment information sensor (13), thereby controlling the air-conditioning operation of the air conditioner (10).

In particular, the control unit (14) according to this embodiment controls the air-conditioning operation (a first air-conditioning operation) of the air conditioner (10) in the room (r1), based on the drowsiness conditions of the users (U1, U2, U3) estimated by the arithmetic unit (60), such that the drowsiness levels of the users (U1, U2, U3) decrease. The air-conditioning operation performed based on results of estimating the drowsiness conditions will be described in detail below.

The control unit (14) preferably includes a neural network constructed in advance, just like an estimator (66) of the arithmetic unit (60) described below. The reason for this is that the air-conditioning operation is to be more finely adjusted.

<Remote Controller>

The remote controller (30) is attached to a wall surface in the room (r1). Although not shown, the remote controller (30) includes a display configured to display various screens, and a plurality of operation buttons configured to accept operations of the users (U1, U2, U3). If a user (U1, U2, U3) operates any one of the operation buttons, the various screens associated with the operation of the user (U1, U2, U3) are displayed on the display. The display shows the set temperature, the set humidity, and other elements of air in the room (r1) as a normal screen.

The remote controller (30) according to this embodiment is capable of accepting the entry, by the user (U1, U2, U3), of the actual drowsiness condition of each user (U1, U2, U3) (i.e., drowsiness information indicating whether or not each user (U1, U2, U3) actually feels drowsy and their drowsiness levels). Based on the entered drowsiness information, the arithmetic unit (60) can determine whether or not the result of estimating the drowsiness condition of the user (U1, U2, U3) matches the actual drowsiness condition of the user (U1, U2, U3). In view of the fact that the air-conditioning operation of the air conditioner (10) is performed based on the result of estimating the drowsiness condition of the user (U1, U2, U3), the entry is preferably made while the air conditioner (10) performs the air-conditioning operation in accordance with the result of estimating the drowsiness condition of the user (U1, U2, U3). However, this is merely a non-limiting example. The entry may be used to correct details of the air conditioning control conducted by the air conditioner (10) in accordance with the estimated result of the drowsiness condition of the user (U1, U2, U3) (for example, may be used to adjust the rotational speed of the indoor fan (12) in accordance with the actual drowsiness condition).

<Configuration of Air-Conditioning Controller>

As shown in FIG. 2, the air-conditioning controller (50) includes the remote controller (30) equivalent to the receiver, and the arithmetic unit (60), in addition to the room environment information sensor (13), the control unit (14), and the camera (26), which are some of the components of the air conditioner (10).

The room environment information sensor (13), the control unit (14), the camera (26), and the remote controller (30) have been described above. Thus, the arithmetic unit (60) will be described below.

<Arithmetic Unit>

The arithmetic unit (60) mainly performs an operation for estimating the drowsiness condition of each user (U1, U2, U3), and is a computer including a storage unit (62) and a CPU (65). The arithmetic unit (60) may be a cloud server, a local server, or any other server.

The arithmetic unit (60) is connected to the air conditioner (10) and the remote controller (30) so as to be capable of communicating with the air conditioner (10) and the remote controller (30) in a wired or wireless manner. Thus, the arithmetic unit (60) can acquire the results sensed by the room environment information sensor (13), such as the temperature of air in the room (r1), and the image taken by the camera (26) from the air conditioner (10). If the remote controller (30) accepts the entry of drowsiness information indicating the actual drowsiness condition from the user (U1, U2, U3), the arithmetic unit (60) can acquire the drowsiness information. The arithmetic unit (60) can output the result estimated by the arithmetic unit (60) itself, i.e., the drowsiness condition, to the control unit (14) of the air conditioner (10).

In this embodiment, a situation where the arithmetic unit (60) is an apparatus different from the air conditioner (10) is exemplified. However, the arithmetic unit (60) may be configured as a microcomputer including a CPU and a memory, just like the control unit (14), and may be incorporated into the air conditioner (10).

The storage unit (62) is configured as a nonvolatile storage device, such as a flash memory or a hard disk. The storage unit (62) mainly stores user information (63).

As shown in FIG. 3, the user information (63) includes the movement and condition (including facial expressions) of each user (U1, U2, U3), and the associated drowsiness condition of the user (U1, U2, U3) who is making the movement and is in the condition. For example, actions and facial expressions, for example, of the users (U1, U2, U3) which the users naturally make while they are drowsy or not drowsy may differ among the users. In other words, for example, actions and facial expressions associated with a sense of drowsiness may have tendencies varying among the users (U1, U2, U3). Thus, definitions of the tendencies as criteria indicating, so to speak, the drowsiness conditions of the users (U1, U2, U3) correspond to the user information (63).

The CPU (65) reads and executes various programs stored in the storage unit (62) and a memory different from the storage unit (62), and functions as the estimator (66) and a model updater (68).

—Estimation of Users' Drowsiness Condition—

The estimator (66) estimates the drowsiness conditions of the users (U1, U2, U3) using the image of the users (U1, U2, U3) taken by the camera (26) and the room environment information indicating the results sensed by the room environment information sensor (13) as essential parameters. Such an estimator (66) includes an estimation model (67).

The estimation model (67) is a dedicated model for determining the drowsiness conditions (drowsiness levels) of the users (U1, U2, U3) based on the taken image or other materials by calculation using a technique such as deep learning, and is previously constructed as a neural network. As indicated by the broken line shown in FIG. 4, the estimation model (67) of this embodiment is, so to speak, a double-layer structure neural network mainly including an image processing neural network (67a) and a drowsiness estimation neural network (67b). The image processing neural network (67a) subjects data of the image taken by the camera (26) to image processing. The drowsiness estimation neural network (67b) estimates the drowsiness conditions of the users (U1, U2, U3) based on information about a result of the image processing and the results sensed by the room environment information sensor (13).

The estimator (66) first enters the data of the image taken by the camera (26) into the image processing neural network (67a). The image processing neural network (67a) extracts movements of the users (U1, U2, U3), such as stretching, and the conditions of the users (U1, U2, U3), such as a condition where their eyes are closed, and determines the sex and age of the users (U1, U2, U3), while making full use of edge detection, contrast processing and other techniques in addition to synchronization processing for image data (here, dynamic image data). In other words, the image processing neural network (67a) extracts specific movements and conditions of the users (U1, U2, U3) representing the drowsiness condition, and determines their sex and age as a factor affecting their drowsiness level.

Figure 5:
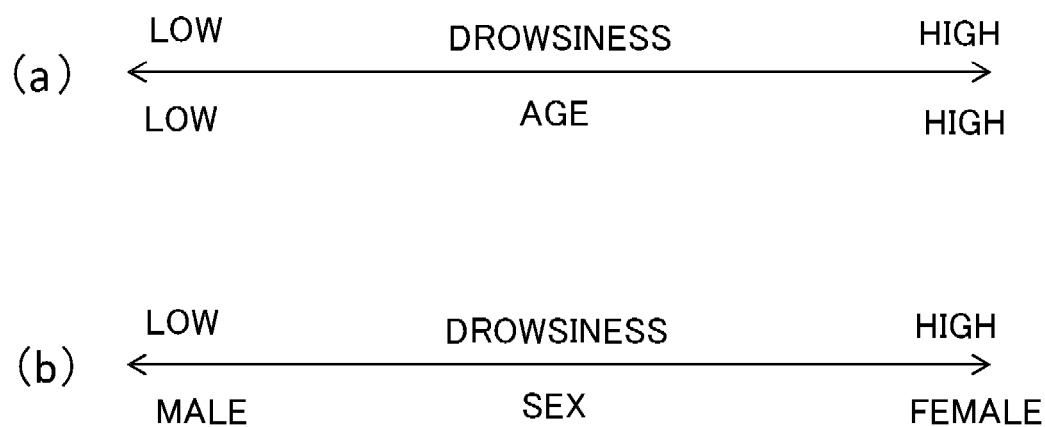
FIG. 5 shows exemplary relations between age and drowsiness and between sex and drowsiness.

A portion (a) of FIG. 5 conceptually shows an example of the relation between age and the drowsiness level. A portion (b) of FIG. 5 conceptually shows an example of the relation between sex and the drowsiness level. The portion (a) of FIG. 5 shows that if the room (r1) has a certain uniform temperature, many younger users (U1, U2, U3) tend not to feel so drowsy, and many older users (U1, U2, U3) tend to feel drowsy. The portion (b) of FIG. 5 shows that if the room (r1) has a certain uniform temperature, females may tend to feel drowsier than males of the same age as the females. As can be seen, the sex and age determined each serve as one of the indexes affecting the drowsiness level.

Figure 4:
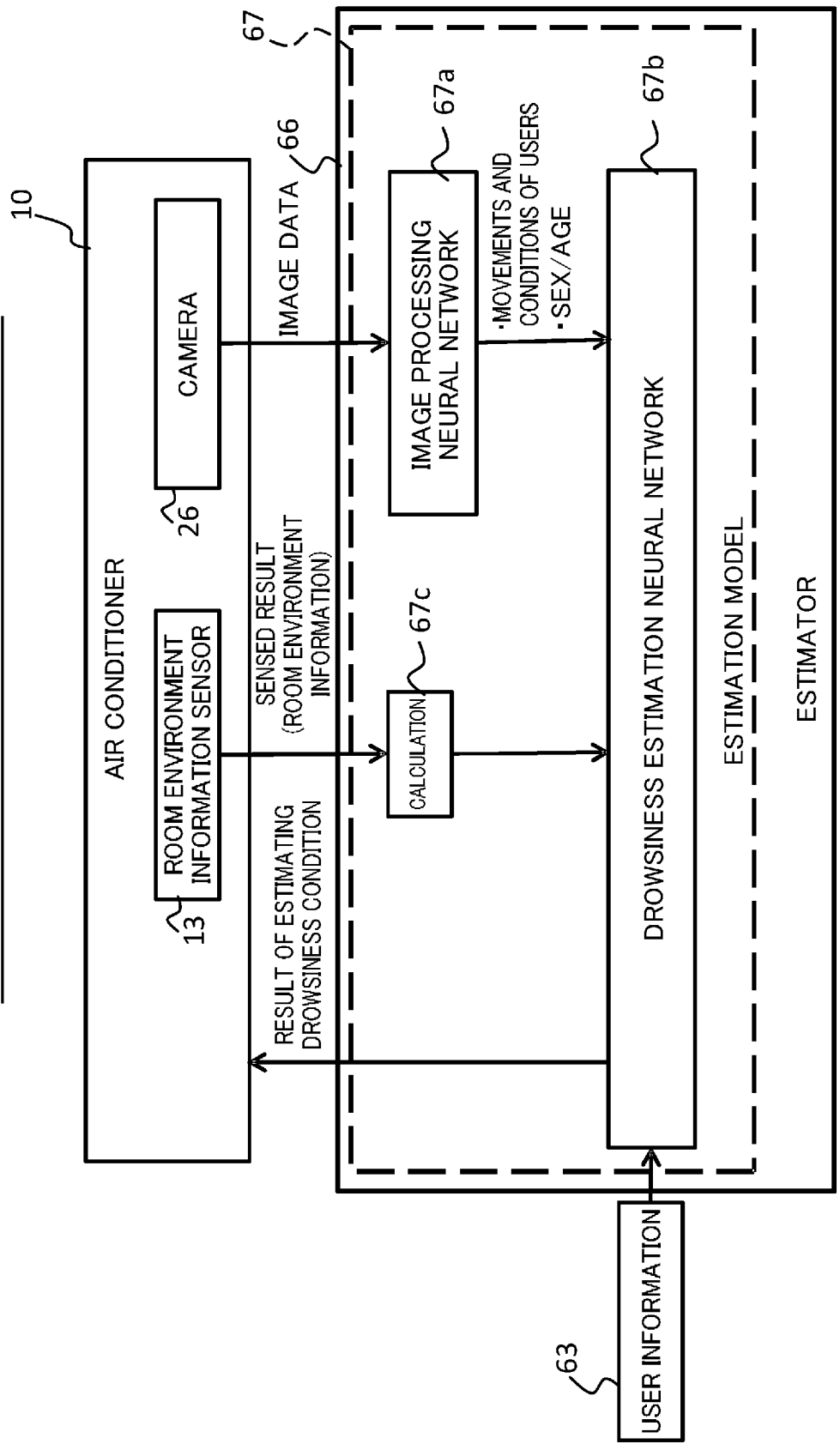
FIG. 4 is a conceptual diagram showing the input and output of an estimation model during estimation of a drowsiness condition according to a first embodiment.

As shown in FIG. 4, the extracted and calculated results output from the image processing neural network (67a), and information about the results sensed by the room environment information sensor (13) (room environment information) such as the temperature, humidity, and $CO_2$ concentration of air in the room (r1) are entered into the drowsiness estimation neural network (67b). In this embodiment, for example, the results sensed by the room environment information sensor (13) are subjected to a predetermined calculation by a calculation neural network (67c) of the estimation model (67) to obtain a type of data that can be treated by the drowsiness estimation neural network (67b), and are then entered, as information about the results sensed by the room environment information sensor (13), into the drowsiness estimation neural network (67b). However, the results may be directly entered into the drowsiness estimation neural network (67b) with the calculation neural network (67c) bypassed.

The drowsiness estimation neural network (67b) determines the drowsiness condition of each user (U1, U2, U3) using the user information (63) shown in FIG. 3 as a reference, based on, out of the entered various pieces of information, the extracted result indicating a specific movement and condition of the user (U1, U2, U3) showing the drowsiness condition and information about the results sensed by the room environment information sensor (13). In this case, the entered calculated results, i.e., the sex and age of the user (U1, U2, U3), are taken into account in calculation of the drowsiness condition of the individual users (U1, U2, U3).

For example, as the temperature and $CO_2$ concentration in the room (r1) increase, the drowsiness of the users (U1, U2, U3) is more easily induced. For this reason, the specific movement and condition of the users (U1, U2, U3) and the information about the results sensed by the room environment information sensor (13) are used to estimate the drowsiness levels of the individual users (U1, U2, U3). Taking the relation between sex or age and the drowsiness level, shown in the portions (a) and (b) of FIG. 5, into consideration allows drowsiness information about each user (U1, U2, U3) to be more finely estimated.

The estimator (66) transmits the drowsiness condition (drowsiness level) of the user (U1, U2, U3) thus determined, as the result of estimating the drowsiness condition, to the control unit (14) of the air conditioner (10).

—Updating of Estimation Model—

Figure 6:
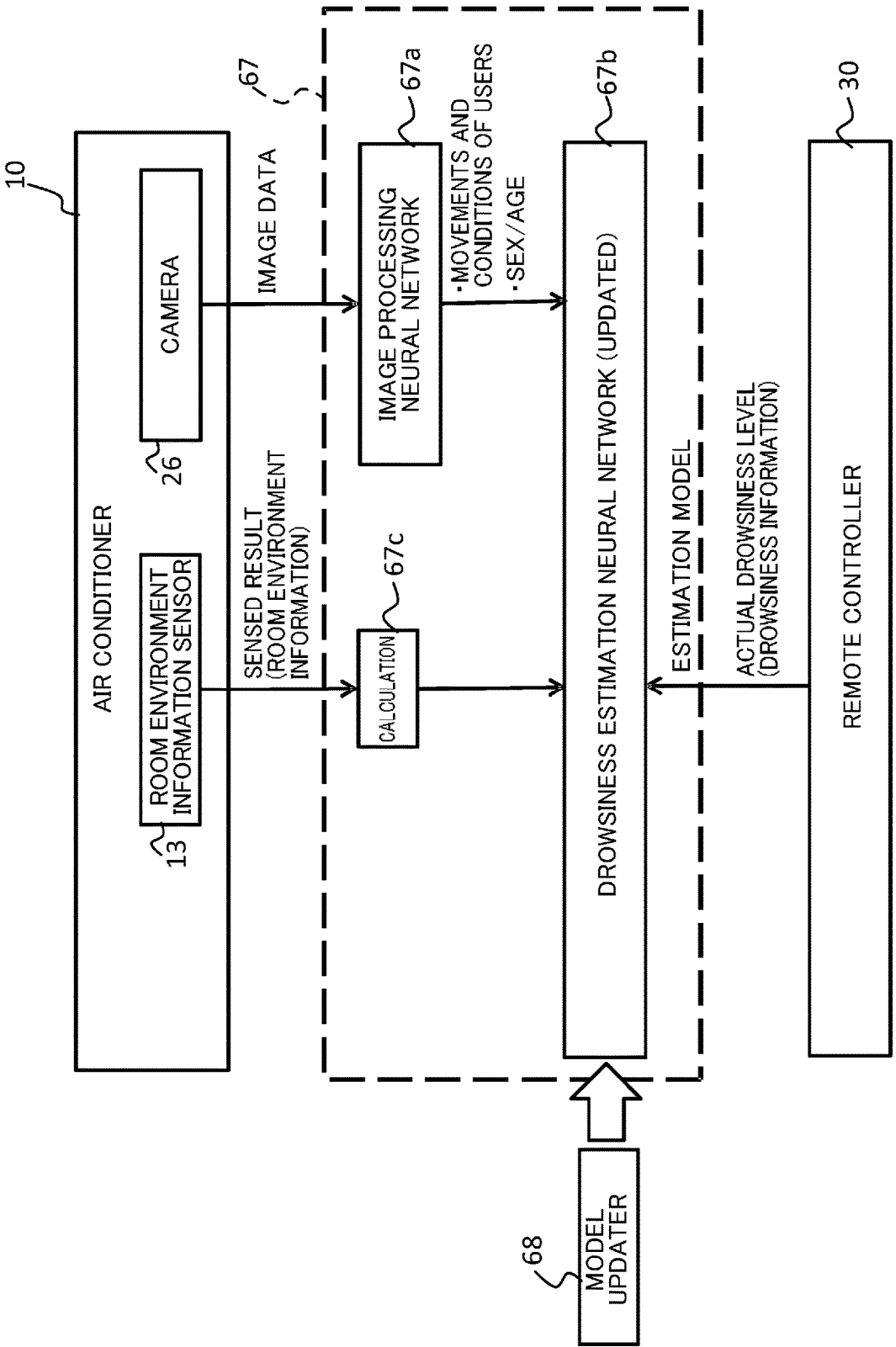
FIG. 6 is a conceptual diagram showing the input and output of the estimation model during updating of the estimation model according to the first embodiment.

As shown in FIG. 6, the model updater (68) makes the estimation model (67) learn based on the data on the image taken by the camera (26) and drowsiness information indicating the actual drowsiness conditions of the users (U1, U2, U3) accepted by the remote controller (30).

A new image taken by the camera (26) after estimation of the drowsiness conditions may show a desired change in the movement and condition of a user (U1, U2, U3) (for example, the user (U1, U2, U3) who had been resting a cheek on a hand stopped resting the cheek on the hand). In this case, a determination can be made that the operation for estimating the drowsiness condition works relatively well and that the air-conditioning operation performed based on the estimated result (i.e., the first air-conditioning operation) helps eliminating the drowsiness condition of the user (U1, U2, U3). However, if such a desired change is not observed, the operation for estimating the drowsiness condition may be different from the actual drowsiness condition. To address this problem, the model updater (68) updates the estimation model (67) using the new image taken by the camera (26).

Non-limiting examples of the movement and condition of a user (U1, U2, U3) representing the drowsiness condition include, in addition to the movement of resting a cheek on a hand, a facial expression, how the user leans the body, whether the user is slow or active in movement, whether or not the user stretches the body, whether the user's eyes are open or closed, and the state during working, as described above. If these movements and conditions also show the desired change representing a reduction in the drowsiness, a determination can be made that the air-conditioning operation performed based on the estimated result (i.e., the first air-conditioning operation) helps eliminating the drowsiness condition of the user (U1, U2, U3). Thus, the model updater (68) updates the estimation model (67).

Specific examples of the movements and conditions based on which it is possible to determine that the drowsiness condition of the user is being eliminated are indicated below.

(I) The number of times of changes in the user's facial expression per fixed period was small before the air-conditioning operation, but increased after the air-conditioning operation.

(II) The user's body leaned to the right or left before the air-conditioning operation, but straightened without leaning after the air-conditioning operation.

(III) The body movement was slow before the air-conditioning operation, but became active after the air-conditioning operation.

(IV) The number of times of stretching of the user was large before the air-conditioning operation, but decreased after the air-conditioning operation.

(V) The user's eyes were closed before the air-conditioning operation, but were opened after the air-conditioning operation.

(VI) The user was not working before the air-conditioning operation, but is doing some work after the air-conditioning operation.

As shown by the specific examples, whether or not the drowsiness condition of the user has been eliminated can be determined not only based on whether or not a certain movement has been made and whether or not a certain condition has arisen, but also based on fluctuations in the frequency of the certain movement and condition. These fluctuations are generally referred to as the "desired change." If such a desired change is observed from the images taken by the camera (26), a determination can be made that the operation for estimating the drowsiness condition generally matches the actual drowsiness condition. Thus, the estimation model (67) is not updated.

The drowsiness information entered by the users (U1, U2, U3) via the remote controller (30) indicates the actual drowsiness levels of the users (U1, U2, U3). For this reason, the model updater (68) updates the estimation model (67) using the drowsiness information accepted by the remote controller (30) as well.

Such an update operation allows the estimation model (67) (specifically, the drowsiness estimation neural network (67b)) to be updated to a model that enables calculation of an estimated result closer to the actual drowsiness condition.

If a desired change is observed as a result of comparison between the movements and conditions of the users (U1, U2, U3) on an image previously taken and the movements and conditions of the users (U1, U2, U3) on a new image taken, and/or if the drowsiness information accepted by the remote controller (30) indicates that the users' drowsiness level becomes lower than their previous drowsiness level by a predetermined or greater number of levels, the model updater (68) determines that an operation for updating the estimation model (67) is not required. Thus, the operation for updating the estimation model (67) does not have to be performed. In other words, the operation for updating the estimation model (67) is recommended to be performed if the desired change in the movements and conditions of the users (U1, U2, U3) is not observed between the image previously taken and the new image taken, and/or if the drowsiness information accepted by the remote controller (30) indicates that the users' drowsiness level is higher than a desired drowsiness level. The reason for this is to avoid unnecessary processing by the CPU (65) and substantially prevent the CPU (65) from being highly loaded.

In this embodiment, a target component of the estimation model (67) to be updated is the drowsiness estimation neural network (67b). However, the image processing neural network (67a) or the calculation neural network (67c) may be a target to be further updated.

As shown in FIG. 6, the results sensed by the room environment information sensor (13) may also be used to update the estimation model (67), but does not have to be used.

<Air-Conditioning Operation Associated With Estimated Drowsiness Condition of User>

Figure 7:
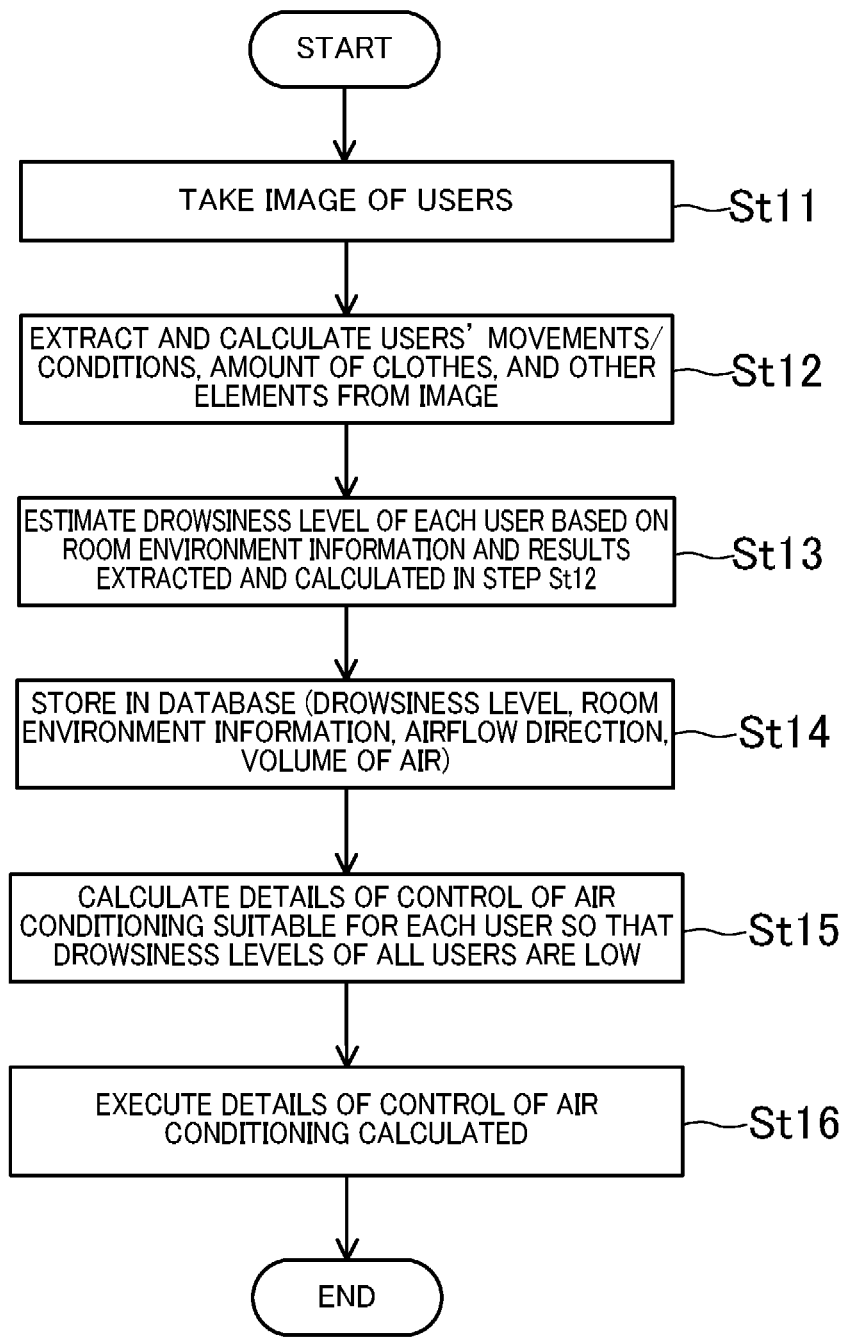
FIG. 7 shows the flowchart of an operation for estimating users' drowsiness conditions and an air-conditioning operation associated with the users' drowsiness conditions.

FIG. 7 shows the flowchart of an operation for estimating the drowsiness conditions of users (U1, U2, U3) and an air-conditioning operation associated with the estimated drowsiness conditions (drowsiness levels).

The camera (26) takes an image of the users (U1, U2, U3) (St11). The image taken by the camera (26) is transmitted to the arithmetic unit (60).

In the arithmetic unit (60), the estimator (66) uses the image processing neural network (67a) of the estimation model (67) to extract the movements and conditions of the users (U1, U2, U3) and determine their sex and age (St12). The estimator (66) enters the extracted and determined results in step St12 and the room environment information (here, information on sensed results) indicating the results sensed by the room environment information sensor (13) into the drowsiness estimation neural network (67b) of the estimation model (67), and estimates the drowsiness conditions of the users (U1, U2, U3) including their drowsiness levels (St13). The results of estimating their drowsiness conditions are transmitted to the control unit (14) of the air conditioner (10).

Although not shown, the estimated results are stored in a database included in the arithmetic unit (60) (St14). At this time, the room environment information including the temperature in the room (r1), and the current airflow direction and volume of air flowing from the air conditioner (10) are stored in the database while being associated with the estimated results. To improve the accuracy of the operation for estimating the drowsiness condition, the database may be used to update the estimation model (67). The database is further preferably used to correct a "threshold value" indicated below to an optimal value.

The control unit (14) of the air conditioner (10) calculates details of air conditioning control suitable for the respective users (U1, U2, U3), so that the estimated drowsiness level is equal to or less than the threshold value (St15), and conducts the air conditioning control calculated (St16). For example, in a case of a greater difference between the estimated drowsiness level and the threshold value, the control unit (14) executes details of air conditioning control in which increased volume of cooled or heated air is supplied to a user (U1, U2, U3) at the estimated drowsiness level. In a case of a smaller difference between the estimated drowsiness level and the threshold value, the control unit (14) executes details of air conditioning control in which the current volume of air supplied to a user (U1, U2, U3) at the estimated drowsiness level is maintained. As can be seen, details of air conditioning control are calculated and executed to change the airflow direction and volume of air flowing toward each user (U1, U2, U3) in accordance with the difference between the drowsiness level of the user (U1, U2, U3) and the threshold value. It can be said that such details of air conditioning control are used to eliminate the drowsiness of a user (U1, U2, U3) whose drowsiness level is high and help the user to become awake, and are used to continuously maintain the current condition of a user (U1, U2, U3) whose drowsiness level is low. Thus, air conditioning control lowers or maintains the drowsiness level of each user. This lowers the average drowsiness level of all the users (U1, U2, U3) in the room (r1), and allows the users (U1, U2, U3) to work more efficiently.

<Advantages>

The room environment affects the drowsiness conditions of the users (U1, U2, U3). Thus, the estimator (66) of the arithmetic unit (60) estimates the drowsiness conditions of the users (U1, U2, U3), based on the image of the users (U1, U2, U3) taken by the camera (26) and the room environment information indicating the results sensed by the room environment information sensor (13) (the temperature and $CO_2$ concentration in the room (r1) and other elements). Thus, the drowsiness of the users (U1, U2, U3) can be accurately determined.

The image shows movements and conditions of the users (U1, U2, U3) representing the drowsiness conditions of the users (U1, U2, U3). Thus, the estimator (66) extracts the movements and conditions of the users (U1, U2, U3) from the image, and estimates the drowsiness conditions of the users (U1, U2, U3). This improves the accuracy with which the drowsiness conditions of the users (U1, U2, U3) are estimated.

In addition, a difference in age and sex may affect a person's sense of "drowsiness." Thus, the estimator (66) determines the age and sex of the users (U1, U2, U3) from the image, and further uses the determined results to estimate the drowsiness conditions of the users (U1, U2, U3). This further improves the accuracy with which the drowsiness conditions of the users (U1, U2, U3) are estimated.

The camera (26) is provided for the air conditioner (10) mounted on the ceiling. This allows the camera (26) to take an image of the users (U1, U2, U3) present in the room (r1) while the possibility that the users may be blocked by an obstacle is reduced.

The estimator (66) estimates the drowsiness condition of each of the users (U1, U2, U3) present in the room (0). In other words, in this embodiment, the drowsiness conditions of the individual users (U1, U2, U3) can be estimated.

Incidentally, the movements and conditions of the users (U1, U2, U3) observed while the users (U1, U2, U3) feel "drowsy" or do not feel "drowsy" may vary among the users (U1, U2, U3). Thus, the estimator (66) uses the user information (63) indicating the movements and conditions observed while the individual users (U1, U2, U3) feel "drowsy" or do not feel "drowsy" to compare the user information (63) with the movements and conditions of the users (U1, U2, U3) in the actually taken image. This further improves the accuracy with which the drowsiness conditions of the individual users (U1, U2, U3) are estimated.

The control unit (14) of the air conditioner (10) controls the air-conditioning operation (the first air-conditioning operation), based on the drowsiness conditions of the users (U1, U2, U3) estimated by the estimator (66) of the arithmetic unit (60), such that their drowsiness level decreases. Thus, even if the users (U1, U2, U3) do not operate the remote controller (30) or any other component to instruct the air conditioner (10) to perform an air-conditioning operation that eliminates their drowsiness, the air conditioner (10) automatically performs an air-conditioning operation suitable for reducing the drowsiness of the users (U1, U2, U3) and awakening them. This improves the convenience of the users (U1, U2, U3), and eliminates the drowsiness condition of the users (U1, U2, U3) and facilitates awakening the users (U1, U2, U3).

In particular, the accuracy with which the drowsiness conditions of the users (U1, U2, U3) are estimated is improved. Thus, performing an air-conditioning operation in accordance with the estimated drowsiness conditions further facilitates eliminating the drowsiness of the users (U1, U2, U3).

In particular, estimating the drowsiness conditions of the individual users (U1, U2, U3) and performing an air-conditioning operation suitable for the drowsiness conditions of the individual users (U1, U2, U3) can lower the drowsiness levels of all the users (U1, U2, U3) present in the room (r1).

The estimation model (67) learns based on the image of the users (U1, U2, U3) and the drowsiness information of the users (U1, U2, U3) accepted by the remote controller (30). Thus, the estimator (66) performing an operation for estimating the drowsiness conditions using the estimation model (67) that has learned further improves the accuracy with which the drowsiness conditions of the users (U1, U2, U3) are estimated.

The estimation model (67) determines the actual drowsiness conditions of the users (U1, U2, U3) based on the image taken by the camera (26) after the air-conditioning operation performed based on the results estimated by the estimator (66), and learns based on the determined results. More specifically, the estimation model (67) learns based on a change in the movements and conditions by which the drowsiness of the users (U1, U2, U3) has been determined, as a result of comparison between the image taken by the camera (26) before the air-conditioning operation (the first air-conditioning operation) based on the results estimated by the estimator (66) and the image taken by the camera (26) after the air-conditioning operation (the first air-conditioning operation). Here, the change in the movements and conditions by which the drowsiness of the users (U1, U2, U3) has been determined means that the frequency of the movements and conditions decreases or that the movements and conditions are not observed. Thus, whether or not the result estimated by the estimation model matches the actual drowsiness condition is more accurately determined. This further improve the accuracy of the estimation model (67) so that the result estimated by the estimation model (67) matches the actual drowsiness condition as much as possible. Performing an operation for estimating the drowsiness conditions of the users (U1, U2, U3) using the estimation model (67) that has learned further improves the accuracy with which the drowsiness conditions of the users (U1, U2, U3) are estimated.

Second Embodiment

In this embodiment, the air-conditioning controller (50) of the first embodiment further includes a thermographic sensor (128) (equivalent to a surface temperature measurer), and the estimator (66) of the first embodiment further uses results sensed by the thermographic sensor (128) to perform the operation for estimating the drowsiness conditions of the users (U1, U2, U3).

Figure 8:
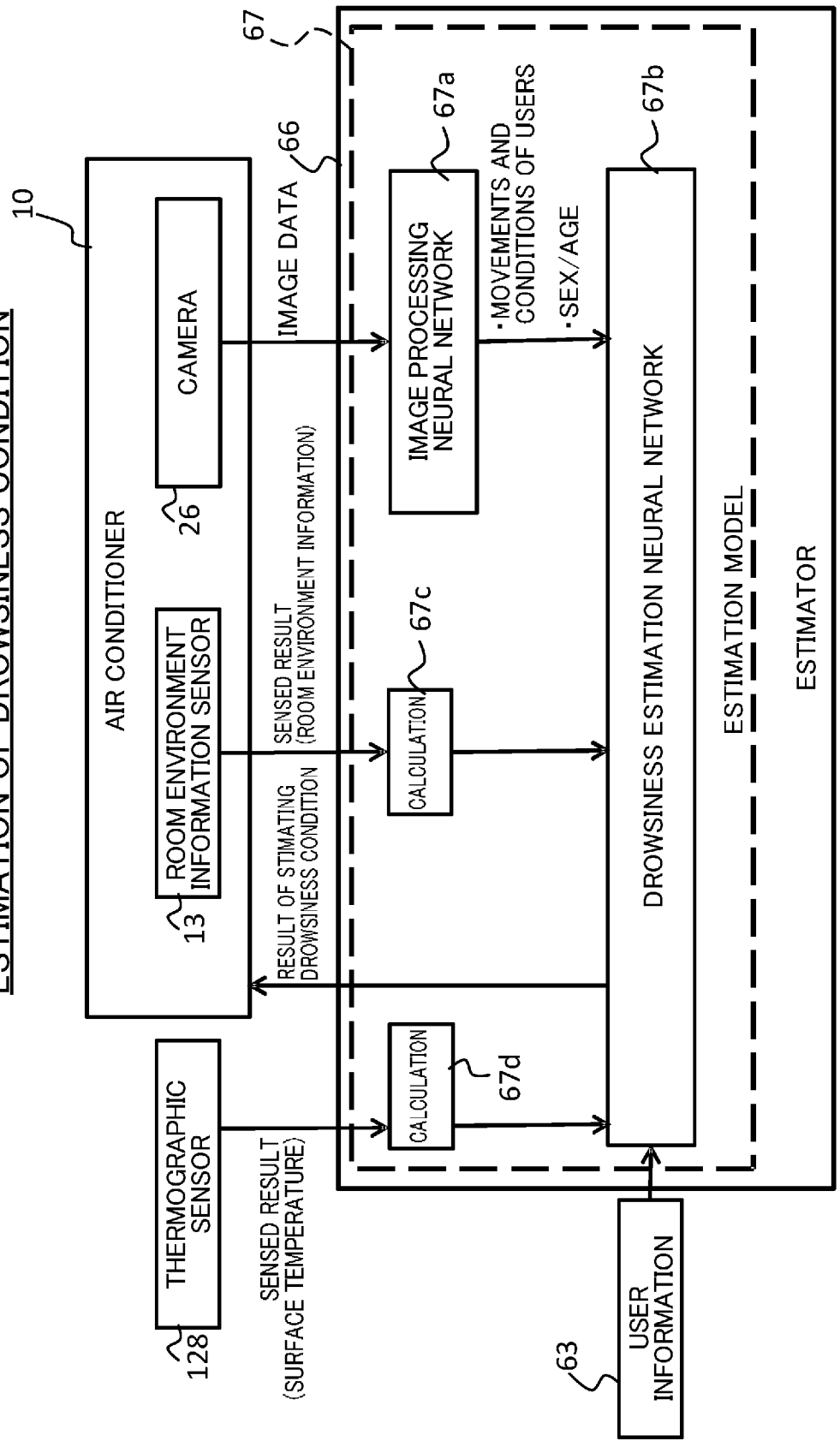
FIG. 8 is a conceptual diagram showing the input and output of an estimation model during estimation of a drowsiness condition according to a second embodiment.

FIG. 8 corresponds to FIG. 4 showing the first embodiment, and is a conceptual diagram showing the input and output of an estimation model (67) during estimation of the drowsiness conditions according to this embodiment. As indicated by the broken line shown in FIG. 8, just like the first embodiment, the estimation model (67) of the estimator (66) is previously constructed as a dedicated neural network for determining, by calculation, the drowsiness conditions of the users (U1, U2, U3), including their drowsiness levels, based on data of the taken image and room environment information. Specifically, the estimation model (67) is, so to speak, a double-layer structure neural network mainly including an image processing neural network (67a) and a drowsiness estimation neural network (67b).

Just like the first embodiment, for example, the room environment information indicating results sensed by a room environment information sensor (13) is subjected to a predetermined calculation by a calculation neural network (67c) of the estimation model (67) to obtain a type of data that can be treated by the drowsiness estimation neural network (67b), and is then entered into the drowsiness estimation neural network (67b).

The input and output of the image processing neural network (67a) are similar to those of the first embodiment.

The drowsiness estimation neural network (67b) receives the results sensed by the thermographic sensor (128) in addition to information about the extracted and calculated results of the image processing neural network (67a) and the results sensed by the room environment information sensor (13).

The thermographic sensor (128) measures the surface temperature of each user (U1, U2, U3) present in a room (r1). A place where the thermographic sensor (128) is to be mounted in the room (r1) should not be limited. The thermographic sensor (128) may be incorporated into a remote controller (30), for example, or may be mounted on a lower surface (21) of the air conditioner (10).

As shown in FIG. 8, just like the results sensed by the room environment information sensor (13) and subjected to calculation by the calculation neural network (67c), the results sensed by the thermographic sensor (128) may be separately subjected to a predetermined calculation by another calculation neural network (67d), and may be then entered into the drowsiness estimation neural network (67b).

Just like the first embodiment, the drowsiness estimation neural network (67b) determines the drowsiness condition of each user (U1, U2, U3), based on the results extracted by the image processing neural network (67a) and the room environment information. In this case, just like the first embodiment, user information (63) is used as a reference. Not only the results calculated by the image processing neural network (67a) (age and sex) but also the results sensed by the thermographic sensor (128) (the surface temperatures) are taken into account to calculate the drowsiness conditions of the users (U1, U2, U3).

Figure 9:
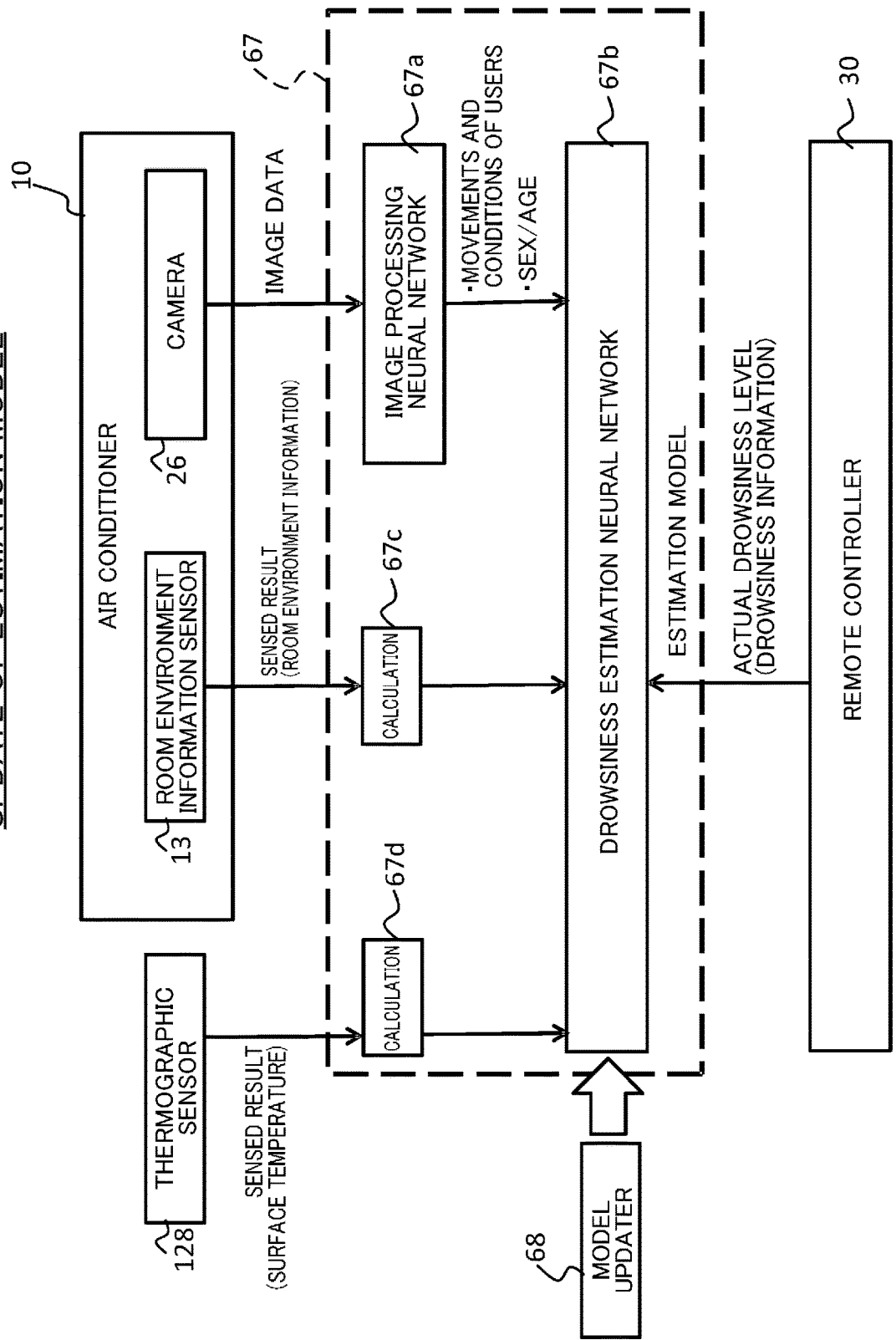
FIG. 9 is a conceptual diagram showing the input and output of the estimation model during updating of the estimation model according to the second embodiment.

As shown in FIG. 9, in addition to information about the results extracted and calculated by the image processing neural network (67a) and the results sensed by the room environment information sensor (13), the results sensed by the thermographic sensor (128) may also be used even in an operation for updating the estimation model (67).

Except for what has been described with reference to FIGS. 8 and 9, specifically, details of a configuration of an air-conditioning system (100) including an air-conditioning controller (50), the user information (63), and an air-conditioning operation using the estimated results are similar to those of the first embodiment, and will not be described.

As can be seen, in this embodiment, the actual surface temperatures of the users (U1, U2, U3) are further used to estimate the drowsiness conditions of the users (U1, U2, U3). This further improves the accuracy with which the drowsiness conditions of the users (U1, U2, U3) are estimated. Furthermore, the air conditioner (10) can perform an air-conditioning operation suitable for further reducing the drowsiness of the users (U1, U2, U3) and awakening them.

The results sensed by the thermographic sensor (128) may also be used by the control unit (14) to determine whether or not the temperature and volume of air to be supplied to the users (U1, U2, U3) from the air conditioner (10) are suitable for the users (U1, U2, U3). For example, supplying a large amount of cooled air to the users (U1, U2, U3) even to improve the drowsiness condition of the users (U1, U2, U3) excessively lowers the surface temperatures of the users (U1, U2, U3) and rather stimulates the users (U1, U2, U3) too much. Thus, if a determination is made based on the results sensed by the thermographic sensor (128) that the temperature and volume of the air to be supplied to the users (U1, U2, U3) by the air conditioner (10) are not suitable for the users (U1, U2, U3), the control unit (14) preferably adjusts details of air conditioning control, based on the results sensed by the thermographic sensor (128), to moderate the temperature and volume of air to be supplied.

Other Embodiments

In the first and second embodiments, air conditioning may be further controlled to eliminate drowsiness in accordance with time of day, using an image and the $CO_2$ concentration included in room environment information. For example, people who have had lunch tend to be drowsy. The higher the $CO_2$ concentration is, the drowsier people are. Thus, it is recommended that the control unit (14) of the air conditioner (10) control a target temperature in a room (r1) such that the target temperature in the afternoon is temporarily lower than that in the morning, and adjust the amount of decrease in the target temperature in accordance with the $CO_2$ concentration. In this case, if the estimator (66) estimates, using the image, that the number of people at a high drowsiness level is greater than or equal to a predetermined number, the control unit (14) preferably determines a ventilation operation to be an air-conditioning operation to reduce the $CO_2$ concentration.

In the first and second embodiments, the estimator (66) may further use the result of sensing the heart rate of each user (U1, U2, U3) to estimate the drowsiness condition of the user (U1, U2, U3).

Specifically, the estimator (66) determines the range of fluctuation in the interbeat intervals of the heart rate, using the result of sensing the heart rate. If this range of fluctuation continues to be less than a predetermined value over a fixed period, the estimator (66) determines that the interbeat intervals of the user (U1, U2, U3) are stable, and that the frequency of the user's heart beats is low. This allows the estimator (66) to estimate that the drowsiness level of the user (U1, U2, U3) is relatively high. In other words, the estimator (66) estimates that the more stable the interbeat intervals are, the higher the drowsiness level of the user (U1, U2, U3) is, whereas the more unstable the interbeat intervals are, the lower the drowsiness level of the user (U1, U2, U3) is.

Thus, the drowsiness level of each user (U1, U2, U3) can be more finely determined. The heart rate of each user (U1, U2, U3) may be calculated, as information indicating the condition of the user (U1, U2, U3), based on the image taken by the camera (26), or may be sensed by a sensor, different from the camera (26), which senses the heart rate. The heart rate of each user (U1, U2, U3) may be used in the learning of the estimation model (67).

The control unit (14) may use the age and sex of the users (U1, U2, U3) determined based on the image in order to control an air-conditioning operation so that individual air-conditioning operations more effective in awaking the respective users are performed.

In the first and second embodiments, a sensor different from the suction sensor may be provided as the room environment information sensor (13). Information about the room sensed by the room environment information sensor (13) includes not only the temperature, humidity, and $CO_2$ concentration in the room (r1) but also various types of information about the environment in the room (r1). The results sensed by the room environment information sensor (13) may include only the temperature in the room (r1), or only the $CO_2$ concentration therein.

Just like the drowsiness information of the users (U1, U2, U3) entered via the remote controller (30), the new image taken by the camera (26) may be used not only to update the estimation model (67) but also to finely adjust, and learn, the control of the air-conditioning operation (equivalent to the first air-conditioning operation).

Fine adjustment and learning of the control of the air-conditioning operation include fine adjustment and learning of target values of the position of the flap (16) and the rotational speed of the indoor fan (12) ([First Specific Example]), the temperature of cold air to which the users (U1, U2, U3) are exposed ([Second Specific Example]), the $CO_2$ concentration ([Third Specific Example]), and the humidity of conditioned air, which are used in the air-conditioning operation for eliminating drowsiness. These specific examples will be described below.

First Specific Example

To accommodate one of the users (U1, U2, U3) who has been estimated by the estimator (66) to be at a drowsiness level higher than or equal to a predetermined level, the control unit (14) of the air conditioner (10) performs control to increase the rotational speed of the indoor fan (12) to a target value and adjust the position of the flap (16). Thus, the air conditioner (10) supplies a larger amount of conditioned air than before to the user (U1, U2, U3) who has been estimated by the estimator (66) to be at the drowsiness level higher than or equal to the predetermined level.

Thereafter, the camera (26) takes a new image. The estimator (66) uses the new image to again estimate the drowsiness level of the user (U1, U2, U3) to which conditioned air is being supplied. As a result, if the drowsiness level of the user (U1, U2, U3) is not lower than a predetermined level, the control unit (14) further increases the rotational speed of the indoor fan (12), and performs control to adjust the position of the flap (16) in accordance with the position of the user (U1, U2, U3). As a result, the air conditioner (10) supplies a larger amount of conditioned air to the user (U1, U2, U3).

Thereafter, the camera (26) again takes a new image. Based on the new image, the estimator (66) again estimates the drowsiness level of the user (U1, U2, U3). If the estimated level becomes lower than the predetermined level, a determination can be made that the drowsiness condition of the user (U1, U2, U3) has been eliminated. In this case, the control unit (14) learns the amount of conditioned air required to eliminate the drowsiness of the user (U1, U2, U3), and sets (increases) the target value to a final value of the rotational speed of the indoor fan (12) to aid in subsequent air-conditioning operations.

As the first specific example, an example in which the airflow direction is controlled through adjustment of the position of the flap (16) while the rotational speed of the indoor fan (12) is adjusted has been described. However, to finely adjust, and learn, an air-conditioning operation for eliminating drowsiness, only control of the airflow direction through adjustment of the flap (16), or only adjustment of the rotational speed of the indoor fan (12) may be finely adjusted, and learned.

Second Specific Example

To accommodate one of the users (U1, U2, U3) who has been estimated by the estimator (66) to be at a drowsiness level higher than or equal to a predetermined level, the control unit (14) of the air conditioner (10) performs control to lower the temperature of conditioned air to a target value and adjust the position of the flap (16). Thus, the air conditioner (10) supplies colder conditioned air than before to the user (U1, U2, U3) who has been estimated by the estimator (66) to be at the drowsiness level higher than or equal to the predetermined level. To lower the temperature of conditioned air to the target value, for example, the control unit (14) controls the air conditioner by temporarily setting a target temperature that is 2° C. lower than the currently set target temperature, thereby performing control to lower the temperature of the conditioned air.

Thereafter, the camera (26) takes a new image. The estimator (66) uses the new image to again estimate the drowsiness level of the user (U1, U2, U3) to which conditioned air is being supplied. As a result, if the drowsiness level of the user (U1, U2, U3) is not lower than a predetermined level, the control unit (14) performs control to further lower the temperature of the conditioned air and to adjust the position of the flap (16) in accordance with the position of the user (U1, U2, U3). As a result, the air conditioner (10) supplies the conditioned air (i.e., cold air having its temperature further lowered) to the user (U1, U2, U3). Specifically, the control unit (14) lowers, by another 2° C., the target temperature which has been temporarily lowered by 2° C., so as to temporarily set the target temperature to be 4° C. lower than the initially set target temperature, thereby controlling the air-conditioning operation of the air conditioner (10).

Thereafter, the camera (26) again takes a new image. Based on the new image, the estimator (66) again estimates the drowsiness level of the user (U1, U2, U3). If the estimated level becomes lower than the predetermined level, a determination can be made that the drowsiness condition of the user (U1, U2, U3) has been eliminated. In this case, the control unit (14) learns how cold the conditioned air required to eliminate the drowsiness of the user (U1, U2, U3) is (i.e., the degree of reduction in the temperature of the conditioned air), and sets (decreases) the target value to a final temperature of the conditioned air so that conditioned air having the set temperature is supplied in subsequent air-conditioning operations.

The control unit (14) may control the air-conditioning operation of the air conditioner (10) to lower the temperature in the entire room (r1) without controlling the position of the flap (16). The humidity of the conditioned air may be adjusted instead of the set temperature of the conditioned air, or the set temperature and humidity of the conditioned air may be adjusted.

Alternatively, the second specific example may be combined with the first specific example.

Third Specific Example

The control unit (14) may further adjust operation of a ventilation fan (not shown) in the room (R1) in accordance with the drowsiness levels of the users (U1, U2, U3) to adjust the $CO_2$ concentration in the room (r1). This adjustment may be further combined with at least one of the first and second specific examples. If this adjustment is combined with the first specific example, the "conditioned air" may be warm air.

Processes for adjusting the $CO_2$ concentration include a process in which if the drowsiness level of a user (U1, U2, U3) is higher than or equal to a predetermined level, the control unit (14) performs at least one of the processes shown in the first and second specific examples, and further operates the ventilation fan (not shown) such that the $CO_2$ concentration is lower than or equal to a predetermined value. In this case, the control unit (14) determines whether or not the period required until the drowsiness condition of the user (U1, U2, U3) is eliminated is shorter than the period required in the case where the ventilation fan (not shown) does not operate (i.e., the case in which only at least one of the processes shown in the first and second specific examples is just performed), and if it is, determines how much the period has been shortened. In addition, the control unit (14) learns, as the target value, the $CO_2$ concentration achieved when the drowsiness is eliminated.

Thus, in the subsequent air-conditioning operations, to eliminate the drowsiness condition of the user (U1, U2, U3), the ventilation fan (not shown) is automatically operated with the $CO_2$ concentration further taken into account. This makes it easy for the next air-conditioning operation (the first air-conditioning operation) to more reliably lower the drowsiness level of the user (U1, U2, U3).

In addition, the control unit (14) may further learn what type of air conditioning operation the air conditioner (10) performs to eliminate the drowsiness condition of individual users (U1, U2, U3) and what type of air conditioning operation the air conditioner (10) performs to eliminate the drowsiness condition of the respective users (U1, U2, U3) according to where the user (U1, U2, U3) is in the room (r1).

In such learning of the air-conditioning control, what is entered via the remote controller (30) by the users (U1, U2, U3) as described in the first and second embodiments (drowsiness information) may be further used. In other words, the control unit (14) may use the drowsiness information entered after the air-conditioning control to determine whether or not the current air-conditioning control is effective for eliminating the drowsiness condition, and may update the target values by learning. In this case, a control model for use in the air-conditioning control may also be constructed and may be made to learn.

In the first and second embodiments, the image shows movements and conditions of the users (U1, U2, U3) representing the drowsiness conditions of the users (U1, U2, U3). However, the image may show at least either the movements or conditions of the users (U1, U2, U3). In this case, the results extracted by the image processing neural network (67a) correspond to at least either the movements or conditions of the users (U1, U2, U3).

The results of determining sex and age of the users (U1, U2, U3) do not have to be used to estimate their drowsiness conditions.

If the sex and age of each user (U1, U2, U3) are used to estimate drowsiness conditions, either the sex or age of the user (U1, U2, U3) may be used to estimate the drowsiness conditions.

The air conditioner (10) should not be limited to an air conditioner mounted on the ceiling of the room (r1), but may be a wall-mounted air conditioner, a floor-standing air conditioner, or any other types of air conditioners.

The camera (26) merely needs to be positioned to be able to take an image of the users (U1, U2, U3) in the room (r1), and does not have to be provided for the air conditioner (10).

For example, the camera (26) may be a web camera on a personal computer of any one of the users (U1, U2, U3).

The air-conditioning controller (50) according to each of the first and second embodiments can also be used even if one user is present in the room (r1).

If a plurality of users are present in the room (r1), the air-conditioning controller (50) may perform control such that the drowsiness condition of not all the users but an optional one or ones of the users is to be estimated.

The estimator (66) does not have to use user information (63) to estimate the drowsiness conditions.

The air-conditioning operation of the air conditioner (10) does not always have to be controlled based on the results of estimating the drowsiness conditions. Thus, the estimator (66) may be a drowsiness estimator that performs only an operation for estimating the drowsiness conditions.

An operation for updating the estimation model (67) does not have to be performed.

In the case of performing the operation for updating the estimation model (67), either the same parameter or different parameters may be used to estimate the drowsiness conditions and to perform the operation for updating the estimation model (67). For example, the parameter used to estimate the drowsiness conditions may be at least one of the image, the temperature and humidity in the room, the temperature and humidity of air blown out of the outlet (24), the volume of air, the airflow direction, or the air conditioning capacity. The parameter used to update the estimation model (67) may be at least one of the image, the temperature and humidity in the room, the air velocity, the radiation temperature, or the $CO_2$ concentration.

In the first and second embodiments, a case in which the constructed estimation model (67) including neural networks is used to estimate the drowsiness conditions has been described. However, the operation for estimating the drowsiness conditions may be performed through execution of a program, for example, without using the estimation model (67).

Instead of the control unit (14), the arithmetic unit (60) may control the air-conditioning operation.

In the first and second embodiments, a case where the receiver receiving the entry of the drowsiness information is the "remote controller (30)" has been exemplified. However, the receiver may be configured as a different device from the remote controller, such as a smartphone, a tablet, or a personal computer. The drowsiness information may be entered via voice input or any other means.

INDUSTRIAL APPLICABILITY

As can be seen from the foregoing description, the present invention is useful for a drowsiness estimation device configured to estimate the drowsiness condition of a user.

DESCRIPTION OF REFERENCE CHARACTERS

10 Air Conditioner
13 Room Environment Information Sensor (Sensor)
14 Control Unit
26 Camera (Imager)
30 Remote Controller (Receiver)
50 Air-conditioning Controller (Sleep Estimator)
62 Storage Unit
63 User Information
67 Estimator
67 Estimation Model
68 Model Updater
U1, U2, U3 User
128 Thermographic Sensor (Surface Temperature Measurer)

The invention claimed is:

1. A drowsiness estimation device comprising:
an imager configured to take a plurality of images of at least one user, the plurality of images comprising a first image and a second image;
a sensor configured to sense room environment information relating to an environment of a room in which the at least one user is present;
a processor to execute a program;
a memory to store the program which, when executed by the processor, the processor performs processes of:
estimating a drowsiness condition of the at least one user, based on at least one of the plurality of images of the at least one user taken by the imager and the room environment information sensed by the sensor; and
making an estimation model, which is used to estimate the drowsiness condition, learn based on a change in a movement and a condition by which the drowsiness of the at least one user has been determined, the change being obtained by comparison between the first image taken by the imager before a first air-conditioning operation of the air conditioner for conditioning air in the room is performed based on the result estimated by the processor, and the second image taken by the imager after the first air-conditioning operation; and
a controller configured to control the first air-conditioning operation of the air conditioner, based on directly using a result of a current level of drowsiness of the at least one user estimated by the processor, so that a level of the drowsiness condition of the at least one user decreases.

2. The device of claim 1, wherein
at least one of the plurality of images shows a movement of the at least one user representing the drowsiness condition of the at least one user and/or a condition of the at least one user representing the drowsiness condition of the at least one user, and
the processor performs processes of:
extracting the movement of the at least one user and/or the condition of the at least one user from the image at least one of the plurality of images, and
estimating the drowsiness condition of the at least one user.

3. The device of claim 1, wherein the processor performs processes of:
determining sex and/or age of the at least one user from at least one of the plurality of images, and further estimating the drowsiness condition of the at least one user based on the determined sex and/or age of the at least one user.

4. The device of claim 1 further comprising:
a surface temperature measurer configured to measure a surface temperature of the at least one user present in the room, wherein
the processor further performs a process of estimating the drowsiness condition of the at least one user, based on a result measured by the surface temperature measurer.

5. The device of claim 1, wherein
an air conditioner is mounted on a ceiling of the room, and the imager is provided for the air conditioner.

6. The device of claim 1, wherein
if the at least one user includes a plurality of users present in the room, the processor performs a process of estimating the drowsiness condition of each of the plurality of users.

7. The device of claim 6 further comprising:
a storage unit configured to store user information about each of the plurality of users, the user information including the movement and/or the condition of the user and the drowsiness condition of the user who is making the movement and/or who is in the condition, the drowsiness condition being associated with the movement and/or the condition of the user, wherein
the processor performs processes of extracting the movement and/or the condition of each of the users from at least one of the plurality of images, and estimating the drowsiness condition of each of the users using the extracted result and the user information.

8. The device of claim 1 further comprising:
a receiver capable of receiving an entry, by the at least one user, of drowsiness information indicating the drowsiness condition of the at least one user; and
wherein the processor performs a process of making the estimation model learn based on at least one of the plurality of images taken by the imager and/or the drowsiness information received by the receiver.

9. The device of claim 1, wherein the processor further performs processes of:
determining the actual drowsiness condition of the at least one user based on the second image taken by the imager after the first air-conditioning operation is performed based on the result estimated by the processor, and making the estimation model learn based on a result of the determination.

10. The device of claim 1, wherein
the change in the movement and the condition by which the drowsiness of the at least one user has been determined means that a frequency of the movement and the condition decreases or that the movement and the condition are not observed.

11. The device of claim 1 further comprising:
a receiver capable of receiving an entry, by the at least one user, of drowsiness information indicating the drowsiness condition of the at least one user, wherein
the controller learns details of control of the first air-conditioning operation, based on the drowsiness information received by the receiver after the first air-conditioning operation performed based on the result estimated by the processor, so that the level of the drowsiness condition of the at least one user decreases.

12. The device of claim 1, wherein
the controller learns details of control of the first air-conditioning operation, based on the second image taken by the imager after the first air-conditioning operation performed based on the result estimated by the processor, so that the level of the drowsiness condition of the at least one user decreases.

13. The device of claim 11, wherein
the details of control of the first air-conditioning operation include adjusting at least one of a rotational speed of an indoor fan of the air conditioner, a position of a flap configured to adjust an airflow direction of air blown from the air conditioner, a set temperature of the air conditioner, or a target $CO_2$ concentration in the room.

14. A drowsiness estimation device comprising:
an imager configured to take an image of at least one user;
a sensor configured to sense room environment information relating to an environment of a room in which the at least one user is present;
a processor to execute a program;
a memory to store the program which, when executed by the processor, the processor performs a process of:
estimating a drowsiness condition of the at least one user, based on the image of the at least one user taken by the imager and the room environment information sensed by the sensor; and
a controller configured to control a first air-conditioning operation of the air conditioner for conditioning air in the room, based on directly using a result of a current level of drowsiness of the at least one user estimated by the processor, so that a level of the drowsiness condition of the at least one user decreases,
wherein the controller learns details of control of the first air-conditioning operation, based on the image taken by the imager after the first air-conditioning operation performed based on the result estimated by the processor, so that the level of the drowsiness condition of the at least one user decreases.

* * * * *